United States Patent
Ambwani (10) Patent No.: US 10,453,196 B2
(45) Date of Patent: Oct. 22, 2019

(54) DETECTION OF STENT STRUTS RELATIVE TO SIDE BRANCHES

(71) Applicant: LightLab Imaging, Inc., Westford, MA (US)

(72) Inventor: Sonal Ambwani, Hopkinton, MA (US)

(73) Assignee: LIGHTLAB IMAGING, INC., Westford, MA (US)

( * ) Notice: Subject to any disclaimer, the term of this patent is extended or adjusted under 35 U.S.C. 154(b) by 0 days.

(21) Appl. No.: 16/199,109

(22) Filed: Nov. 23, 2018

(65) Prior Publication Data

US 2019/0096063 A1    Mar. 28, 2019

Related U.S. Application Data

(63) Continuation of application No. 14/975,462, filed on Dec. 18, 2015, now Pat. No. 10,140,712.

(Continued)

(51) Int. Cl.
*G06T 7/00* (2017.01)
*A61B 5/00* (2006.01)

(52) U.S. Cl.
CPC .......... *G06T 7/0014* (2013.01); *A61B 5/0084* (2013.01); *A61B 5/4851* (2013.01); *A61B 5/6852* (2013.01); *G06T 7/0012* (2013.01); *A61B 5/0066* (2013.01); *A61B 5/6862* (2013.01); *G06T 2207/10068* (2013.01); *G06T 2207/10101* (2013.01); *G06T 2207/30101* (2013.01)

(58) Field of Classification Search
CPC ...... G02B 6/32; G02B 6/3821; G02B 6/3882; G02B 6/3885; G02B 6/3886; G02B 6/3893; G02B 6/3897; G02B 6/403; G02B 6/4206; G02B 6/4292; G02B 6/43; A61B 5/0066; A61B 5/0084; A61B 5/4851; A61B 5/6852; A61B 5/6862; G06T 2207/10068; G06T 2207/10101; G06T 2207/30101; G06T 7/0012; G06T 7/0014

See application file for complete search history.

(56) References Cited

U.S. PATENT DOCUMENTS 5,054,492 A    10/1991    Scribner et al.
5,321,501 A    6/1994    Swanson et al.
(Continued)

FOREIGN PATENT DOCUMENTS

WO    2006076409    7/2006
WO    2007002685    1/2007
(Continued)

OTHER PUBLICATIONS

Wang et al., "Automatic stent strut detection in intravascular optical coherence tomographic pullback runs", The Int J Cardiovasc Imaging, (2013) 29:29-38, (10 pages).
(Continued)

*Primary Examiner* — Manuchehr Rahmjoo
(74) *Attorney, Agent, or Firm* — K&L Gates LLP (57) ABSTRACT

In part, the disclosure relates to methods of stent strut detection relative to a side branch region using intravascular data. In one embodiment, detecting stent struts relative to jailed side branches is performed using a scan line-based peak analysis. In one embodiment, false positive determinations relating to stent struts are analyzed using a model strut.

19 Claims, 9 Drawing Sheets

Related U.S. Application Data (60) Provisional application No. 62/257,185, filed on Nov. 18, 2015.

(56) References Cited

U.S. PATENT DOCUMENTS

| | | | |
|---|---|---|---|
| 5,459,570 A | 10/1995 | Swanson et al. |
| 5,465,147 A | 11/1995 | Swanson |
| 5,477,858 A | 12/1995 | Norris et al. |
| 5,488,674 A | 1/1996 | Burt et al. |
| 5,509,093 A | 4/1996 | Miller et al. |
| 5,531,227 A | 7/1996 | Schneider |
| 5,619,368 A | 4/1997 | Swanson |
| 5,662,109 A | 9/1997 | Hutson |
| 5,748,598 A | 5/1998 | Swanson et al. |
| 5,771,895 A | 6/1998 | Slager |
| 5,784,352 A | 7/1998 | Swanson et al. |
| 5,797,849 A | 8/1998 | Vesely et al. |
| 5,956,355 A | 9/1999 | Swanson et al. |
| 5,989,189 A | 11/1999 | LeBlanc et al. |
| 6,111,645 A | 8/2000 | Tearney et al. |
| 6,134,003 A | 10/2000 | Tearney et al. |
| 6,148,095 A | 11/2000 | Prause et al. |
| 6,160,826 A | 12/2000 | Swanson et al. |
| 6,191,862 B1 | 2/2001 | Swanson et al. |
| 6,208,883 B1 | 3/2001 | Holupka et al. |
| 6,282,011 B1 | 8/2001 | Tearney et al. |
| 6,421,164 B2 | 7/2002 | Tearney et al. |
| 6,445,939 B1 | 9/2002 | Swanson et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,706,004 B2 | 3/2004 | Tearney et al. |
| 6,879,851 B2 | 4/2005 | McNamara et al. |
| 6,891,984 B2 | 5/2005 | Petersen et al. |
| 7,208,333 B2 | 4/2007 | Flanders et al. |
| 7,231,243 B2 | 6/2007 | Tearney et al. |
| 7,241,286 B2 | 7/2007 | Atlas |
| 7,397,935 B2 | 7/2008 | Kimmel et al. |
| 7,414,779 B2 | 8/2008 | Huber et al. |
| 7,415,049 B2 | 8/2008 | Flanders et al. |
| 7,593,559 B2 | 9/2009 | Toth et al. |
| 7,619,646 B2 | 11/2009 | Freifeld et al. |
| 7,625,366 B2 | 12/2009 | Atlas |
| 7,729,746 B2 | 6/2010 | Redel et al. |
| 7,801,343 B2 | 9/2010 | Unal et al. |
| 7,813,609 B2 | 10/2010 | Petersen et al. |
| 7,848,791 B2 | 12/2010 | Schmitt et al. |
| 7,916,387 B2 | 3/2011 | Schmitt et al. |
| 7,935,060 B2 | 5/2011 | Schmitt et al. |
| 8,116,605 B2 | 2/2012 | Petersen et al. |
| 8,206,377 B2 | 6/2012 | Petroff |
| 8,298,147 B2 | 10/2012 | Huennekens et al. |
| 8,325,419 B2 | 12/2012 | Schmitt |
| 8,358,461 B2 | 1/2013 | Huber et al. |
| 8,412,312 B2 | 4/2013 | Judell et al. |
| 8,449,468 B2 | 5/2013 | Petersen et al. |
| 8,478,384 B2 | 7/2013 | Schmitt et al. |
| 8,478,387 B2 | 7/2013 | Xu |
| 8,503,844 B2 | 8/2013 | Petersen et al. |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,687,201 B2 | 4/2014 | Adler |
| 8,786,336 B1 | 7/2014 | Schmitt |
| 8,831,321 B1 | 9/2014 | Elbasiony |
| 8,948,228 B2 | 2/2015 | Adler |
| 8,953,911 B1 | 2/2015 | Xu et al. |
| 8,983,580 B2 | 3/2015 | Boppart et al. |
| 9,069,396 B2 | 6/2015 | Adler et al. |
| 9,173,591 B2 | 11/2015 | Elbasiony et al. |
| 9,351,698 B2 | 5/2016 | Dascal et al. |
| 9,404,731 B2 | 8/2016 | Adler et al. |
| 9,435,956 B1 | 9/2016 | Xu et al. |
| 9,488,464 B1 | 11/2016 | Schmitt |
| 2002/0115931 A1 | 8/2002 | Strauss et al. |
| 2002/0161351 A1 | 10/2002 | Samson et al. |
| 2005/0201662 A1 | 9/2005 | Petersen et al. |
| 2005/0238067 A1 | 10/2005 | Choi |
| 2006/0095065 A1 | 5/2006 | Tanimura et al. |
| 2006/0165270 A1 | 7/2006 | Borgert et al. |
| 2006/0187537 A1 | 8/2006 | Huber et al. |
| 2006/0203859 A1 | 9/2006 | Cable et al. |
| 2006/0241465 A1 | 10/2006 | Huennekens et al. |
| 2006/0244973 A1 | 11/2006 | Yun et al. |
| 2007/0293932 A1 | 12/2007 | Zilla et al. |
| 2008/0100612 A1 | 5/2008 | Dastmalchi et al. |
| 2009/0027051 A1 | 1/2009 | Stuber et al. |
| 2009/0174931 A1 | 7/2009 | Huber et al. |
| 2009/0204134 A1 | 8/2009 | Kassab |
| 2009/0306520 A1 | 12/2009 | Schmitt et al. |
| 2010/0076320 A1 | 3/2010 | Petersen et al. |
| 2011/0071404 A1 | 3/2011 | Schmitt et al. |
| 2011/0101207 A1 | 5/2011 | Schmitt |
| 2011/0157686 A1 | 6/2011 | Huber et al. |
| 2011/0190586 A1 | 8/2011 | Kemp |
| 2011/0228280 A1 | 9/2011 | Schmitt et al. |
| 2011/0257545 A1 | 10/2011 | Suri |
| 2012/0075638 A1 | 3/2012 | Rollins et al. |
| 2012/0238869 A1 | 9/2012 | Schmitt et al. |
| 2012/0250028 A1 | 10/2012 | Schmitt et al. |
| 2012/0310081 A1 | 12/2012 | Adler et al. |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0051728 A1 | 2/2013 | Petroff |
| 2013/0072805 A1 | 3/2013 | Schmitt et al. |
| 2013/0303910 A1 | 11/2013 | Hubbard et al. |
| 2013/0310698 A1 | 11/2013 | Judell et al. |
| 2014/0018669 A1 | 1/2014 | Xu |
| 2014/0024931 A1 | 1/2014 | Winston et al. |
| 2014/0094697 A1 | 4/2014 | Petroff et al. |
| 2014/0100449 A1 | 4/2014 | Begin et al. |
| 2014/0114182 A1 | 4/2014 | Petersen et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0187929 A1 | 7/2014 | Schmitt et al. |
| 2014/0218742 A1 | 8/2014 | Adler |
| 2014/0249407 A1 | 9/2014 | Adler et al. |
| 2014/0268167 A1 | 9/2014 | Friedman et al. |
| 2014/0276011 A1 | 9/2014 | Schmitt et al. |
| 2014/0276020 A1 | 9/2014 | Hutchins et al. |
| 2014/0309536 A1 | 10/2014 | Douk et al. |
| 2014/0379269 A1 | 12/2014 | Schmitt |
| 2015/0153157 A1 | 6/2015 | Schmitt et al. |
| 2015/0119707 A1 | 7/2015 | Schmitt |
| 2015/0192405 A1 | 7/2015 | Schmitt |
| 2015/0297373 A1 | 10/2015 | Schmitt et al. |
| 2015/0370229 A1 | 12/2015 | Adler et al. |
| 2016/0000406 A1 | 1/2016 | Petroff |
| 2016/0022208 A1 | 1/2016 | Gopinath |
| 2016/0058307 A1 | 3/2016 | Svanerudh |
| 2016/0070066 A1 | 3/2016 | Schmitt et al. |
| 2016/0073885 A1 | 3/2016 | Adler |
| 2016/0174925 A1 | 6/2016 | Dascal et al. |
| 2016/0313507 A1 | 10/2016 | Adler et al. |
| 2016/0335763 A1 | 11/2016 | Ambwani et al. |
| 2016/0335766 A1 | 11/2016 | Ambwani et al. |
| 2017/0024532 A1* | 1/2017 | Gopinath ............... A61B 34/10 |

FOREIGN PATENT DOCUMENTS

| | | |
|---|---|---|
| WO | 2011038044 | 3/2011 |
| WO | 2014092755 | 6/2014 |

OTHER PUBLICATIONS

International Search Report and Written Opinion for International application No. PCT/US2016/062213, mailed from the International Searching Authority dated Jan. 30, 2017 (12 pages).

(56) References Cited

OTHER PUBLICATIONS

International Search Report and Written Opinion of the International Searching Authority for International Application No. PCT/US2013/029855 dated Jun. 17, 2013 (10 pages).
International Search Report and Written Opinion of the International Search Authority for International patent application No. PCT/US2015/042083 dated Oct. 21, 2015 (9 pages).
Bonnema et al., "An automatic algorithm for detecting stent endothelialization from volumetric optical coherence tomography datasets", Physics in Medicine and Biology, 53:12, Jun. 21, 2008, pp. 3083-3098.
Unal et al., "Stent implant follow-up in intravascular optical coherence tomography images", Int J Cardiovasc Imaging, DOI 10.1007/s10554-009-9508-4, published online Sep. 24, 2009, 8 pages.
Xu et al., "Characterization of atherosclerosis plaques by measuring both backscattering and attenuation coefficients in optical coherence tomogrpahy", Journal of Biomedical Optics, 13:3, May/Jun. 2008, 8 pages.
Takano et al., "Evaluation by Optical Coherence Tomography of Neointimal Coverage of Sirolimus-Eluting Stent Three Months After Implantation", American Journal of Cardiology, vol. 99, No. 8, Apr. 14, 2007, pp. 1033-1038.
International Search Report for International Application No. PCT/US2009/060714, dated Jan. 4, 2010, 6 pages.
Written Opinion of the International Searching Authority for International Application No. PCT/US2009/060714, dated Jan. 4, 2010, 6 pages.
English translation of Office Action of Japanese Patent Office dated Feb. 25, 2014 (6 pages).

* cited by examiner

DETECTION OF STENT STRUTS RELATIVE TO SIDE BRANCHES

CROSS-REFERENCE TO RELATED APPLICATIONS

This application is a continuation of U.S. patent application Ser. No. 14/975,462, filed on Dec. 18, 2015, which claims priority to and the benefit of U.S. Provisional Patent Application No. 62/257,185 filed on Nov. 18, 2015, the disclosures of which are herein incorporated by reference in their entirety.

FIELD

The invention relates to systems and methods for stent detection.

BACKGROUND

Interventional cardiologists incorporate a variety of diagnostic tools during catheterization procedures in order to plan, guide, and assess therapies. Fluoroscopy is generally used to perform angiographic imaging of blood vessels. In turn, such blood vessel imaging is used by physicians to diagnose, locate and treat blood vessel disease during interventions such as bypass surgery or stent placement. Intravascular imaging technologies such as optical coherence tomography (OCT) are also valuable tools that can be used in lieu of or in combination with fluoroscopy to obtain high-resolution data regarding the condition of the blood vessels for a given subject.

Intravascular optical coherence tomography is a catheter-based imaging modality that uses light to peer into coronary artery walls and generate images for study. Utilizing coherent light, interferometry, and micro-optics, OCT can provide video-rate in-vivo tomography within a diseased vessel with micrometer level resolution. Viewing subsurface structures with high resolution using fiber-optic probes makes OCT especially useful for minimally invasive imaging of internal tissues and organs, as well as implanted medical devices such as stents.

Stents are a common intervention for treating vascular stenoses. It is critical for a clinician to develop a personalized stent plan that is customized to the patient's vascular anatomy to ensure optimal outcomes in intravascular procedures. Stent planning encompasses selecting the length, diameter, and landing zone for the stent with an intention to restore normal blood flow to the downstream tissues. However, flow-limiting stenoses are often present in the vicinity of vascular side branches. Side branches can be partially occluded or "jailed" during deployment of a stent intended to address a stenosis in the main vessel. Since side branches are vital for carrying blood to downstream tissues, jailing can have an undesired ischemic impact and also can lead to thrombosis. The ischemic effects of jailing are compounded when multiple side branches are impacted or when the occluded surface area of a single branch is increased.

Metal stent detection methods typically detect individual stent struts by detecting shadows cast by the struts onto the blood vessel wall, followed by detecting the location of the struts within the detected shadows. However, struts over jailed side branches are difficult to detect via this method. Side branches appear as large shadows in images because the scan line can be perpendicular to the side branch opening. As a result, it is difficult or impossible to detect strut shadows overlying side branches. Consequently, jailing struts are easily missed by the shadow based detection methods.

The present disclosure addresses the need for enhanced detection of jailing stent struts.

SUMMARY OF DISCLOSURE

Disclosed herein are systems and methods for detecting and visualizing stent struts that occlude, or jail, blood vessel side branches. The systems and methods disclosed herein detect jailing struts by analyzing side branches for sparse intensity peaks. In one embodiment, sparse intensity peaks include scan line intensity peaks that are surrounded by dark regions. The sparse intensity peaks can be identified on optical coherence tomography (OCT) scan lines. The peak corresponds to a potential strut, and the dark regions correspond to the underlying side branch lumen, which appears as a void. Scan lines with potential strut peaks are analyzed to determine whether the scan lines fit an intensity profile consistent with a jailing strut. In one embodiment, consecutive scan lines with potential strut peaks are analyzed to determine whether the scan lines fit an intensity profile consistent with a jailing strut.

In one embodiment, the systems and methods described herein identify a side branch and identify a potential strut at a particular location within the side branch. In one embodiment, the particular location is line-offset. The system and associated side branch detection or other associated software module can then create a model strut at that same location.

In part, the disclosure relates to a method of detecting a stent strut in a representation of a blood vessel. The method includes storing, in memory accessible by an intravascular diagnostic system, intravascular data comprising a first group of scan lines; detecting side branches in the intravascular data; identifying a second group of scan lines within one or more of the detected side branches; determining a peak intensity for each scan line in the second group of scan lines; identifying a third group of scan lines in the second group having a peak intensity less than or equal to a threshold T, wherein the third group comprises one or more scan lines of a detected side branch that are candidates for comprising stent strut image data; and validating the candidates to identify one or more scan lines that comprise stent strut data.

In one embodiment, the validating step comprises determining if each candidate is a false positive for comprising stent strut image data. In one embodiment, the validating step comprises comparing the candidate stent strut image data to model stent strut image data using a correlation factor. In one embodiment, the correlation factor is a linear correlation coefficient. In one embodiment, determining if each candidate is a false positive for comprising stent strut image data comprises comparing the detected candidate stent strut image data to model stent strut image data.

In one embodiment, after determining a peak intensity for each scan line, the method comprises a partitioning the scan lines for a side branch into samples. In one embodiment, the method further includes a step of clustering neighboring scan lines that are contiguous, before validating against the model strut.

In one embodiment, the method further includes the step of adding a validated strut to a list of detected struts. In one embodiment, if the number of samples having an intensity>peak-at-line intensity is greater than threshold T for a candidate strut, discarding the candidate strut or the scan line comprising the candidate strut. In one embodiment, the method further includes determining a start frame and an end frame for each side branch.

In part, the disclosure relates to an automatic processor-based system for detecting a stent strut in a representation of a blood vessel. The system includes one or more memory devices; and a computing device in communication with the memory device, wherein the memory device comprises instructions executable by the computing device to cause the computing device to: store, in memory accessible by an intravascular diagnostic system, intravascular data comprising a first group of scan lines; detect side branches in the intravascular data; identify a second group of scan lines within one or more of the detected side branches; determine a peak intensity for each scan line in the second group of scan lines; identify a third group of scan lines in the second group having a peak intensity less than or equal to a threshold T, wherein the third group comprises one or more scan lines of a detected side branch that are candidates for comprising stent strut image data; and validate the candidates to identify one or more scan lines that comprise stent strut data. instructions to validate step comprises determining if each candidate is a false positive for comprising stent strut image data.

In one embodiment, the method includes instructions to validate step comprises comparing the candidate stent strut image data to model stent strut image data using a correlation factor. In one embodiment, the correlation factor is a linear correlation coefficient. In one embodiment, the computing device comprises further instructions to cause the computing device to determine if each candidate is a false positive for comprising stent strut image data comprises comparing the detected candidate stent strut image data to model stent strut image data. In one embodiment, after determining a peak intensity for each scan line, the computing device comprises further instructions to cause the computing device to partition the scan lines for a side branch into samples.

In one embodiment, the computing device comprises further instructions to cause the computing device to cluster neighboring scan lines that are contiguous, before validating against the model strut. In one embodiment, the computing device comprises further instructions to cause the computing device to adding a validated strut to a list of detected struts.

In one embodiment, if the number of samples having an intensity>peak-at-line intensity is greater than threshold T for a candidate strut, discarding the candidate strut or the scan line comprising the candidate strut. In one embodiment, the computing device comprises further instructions to cause the computing device to determine a start frame and an end frame for each side branch.

BRIEF DESCRIPTION OF DRAWINGS

The figures are not necessarily to scale, emphasis instead generally being placed upon illustrative principles. The figures are to be considered illustrative in all aspects and are not intended to limit the invention, the scope of which is defined only by the claims.

DETAILED DESCRIPTION

The systems and methods disclosed herein describe detecting and analyzing features of an artery using intravascular data including scan lines and images generated using scan lines or other data obtained with regard to the artery. In one embodiment, the intravascular data is analyzed and transformed to detect metal stent struts that block, cage, or otherwise "jail" a side branch of an artery. The intravascular data can include, for example, optical coherence tomography (OCT) or intravascular ultrasound (IVUS) data or other images of a blood vessel of interest. The intravascular data can be analyzed to identify sparse intensity peaks along each scan line—i.e., peaks that are surrounded by dark regions corresponding to a side branch which appears as a large shadow in most cases. In many cases a side branch manifests as an opening of the tissue region in the 2-D cross sectional view. As a consequence of this, there will be no shadows cast by the struts which jail the side branch.

In one embodiment, a sparse peak is characterized by analyzing image statistics along the scan line to check if there is evidence of a bright signal against a dark background. A threshold T or $T_s$, also referred to as a naïve peak at line measurement threshold is then applied on the image statistics to check if the scan lines are candidates for a potential metal strut. Consecutive scan lines, or portions thereof, are analyzed to determine whether they fit an intensity profile consistent with a metal strut in one embodiment. Other thresholds and metrics can be used to filter and select side branch associated scan lines to identify candidates for subsequent validation. In some implementations further validation after scan line identification is not required.

Figure 1A:
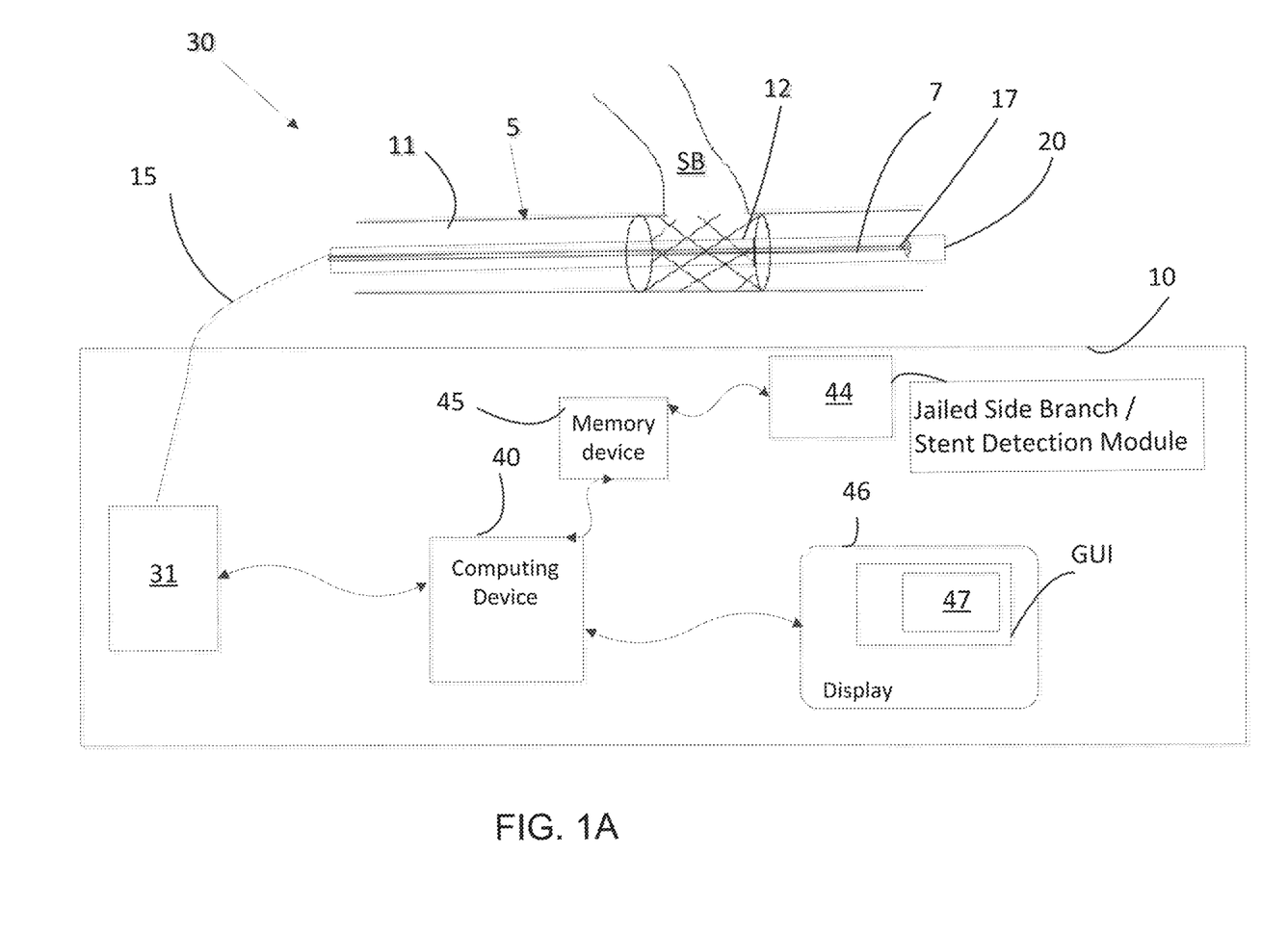
FIG. 1A is an exemplary intravascular data collection system and an associated intravascular data collection probe and related image processing, detection, and other software components according to an illustrative embodiment of the disclosure.

FIG. 1A is a high level schematic diagram depicting a blood vessel 5, such as an artery, a data collection probe 7 and an intravascular data collection and processing system 10. The system 10 can include for example, an OCT, IVUS, or other intravascular imaging system. A stent 12 is shown in the blood vessel 5 positioned such that is jails or blocks a side branch SB. The system 10 can include various software modules suitable for performing side branch detection, peak detection, error correction, model comparisons, lumen detection, and various other processes as described herein. The system 10 can include a suitable light source that satisfies the coherence and bandwidth requirements of the applications and data collection described herein. The system 10 can include an ultrasound imaging system. The probe 7 can include a catheter 20 having a catheter portion having one or more optical fibers 15 and a probe tip 17 disposed therein. The probe tip 17 includes a beam director in one embodiment.

As shown, the catheter 20 is introduced into the lumen 11 such as an arterial lumen. The probe 7 can include a rotating or slidable fiber 15 that directs light forward into the lumen 14 or at a direction perpendicular to the longitudinal axis of the fiber 15. As a result, in the case of light that is directed from the side of the probe as the fiber 15 rotates, OCT data is collected with respect to the walls of the blood vessel 5. The walls of the blood vessel 5 define a lumen boundary. This lumen boundary can be detected using the distance measurements obtained from the optical signals collected at the probe tip 17 using lumen detection software component. Side branches and stent struts and other features can be identified in the scan lines generated during a pullback through the artery by the probe. The probe 7 can include other imaging modalities in addition to OCT such as ultrasound in one embodiment.

Figure 1B:
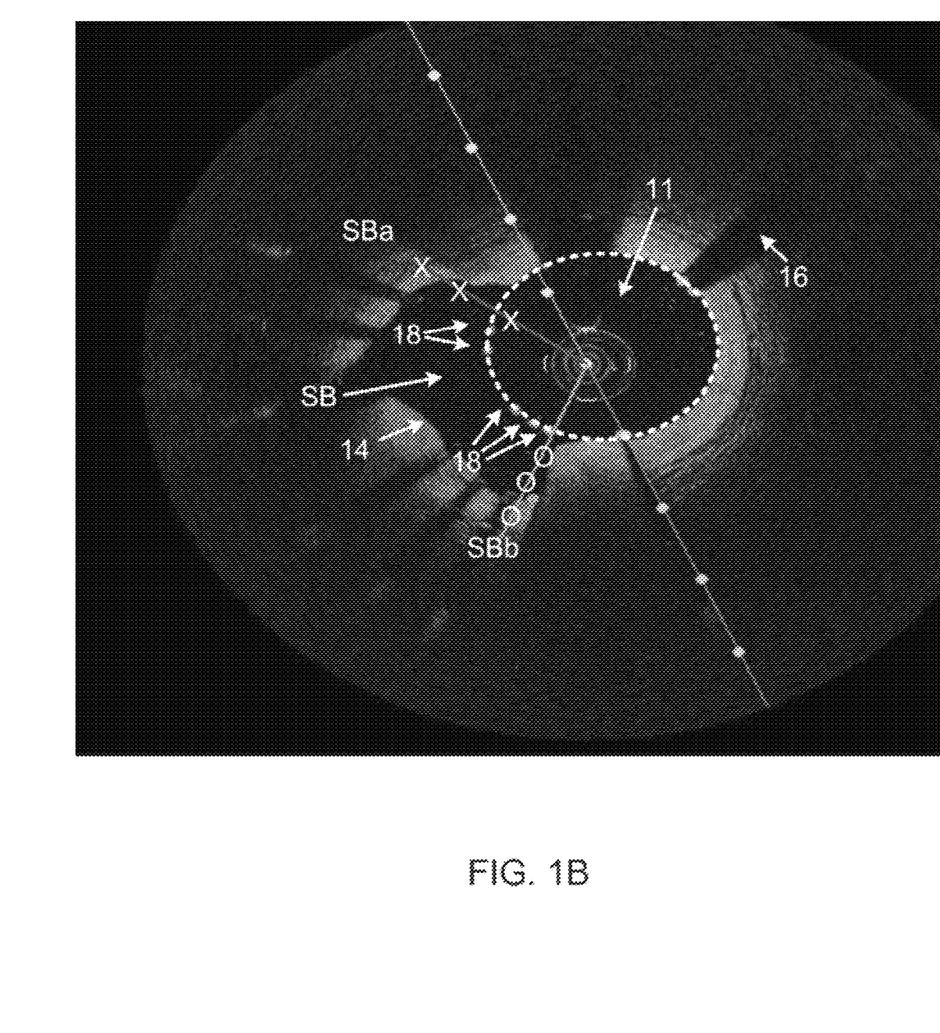
FIG. 1B is a cross-sectional OCT image of a stented blood vessel according to an illustrative embodiment of the disclosure.

As shown in FIG. 1A, the probe tip 17 is positioned in the lumen 11 such that it is distal to a stented region of the blood vessel 5. The probe tip 17 is configured to transmit light and receive backscattered light from objects, such as for example stent 12, and wall of the blood vessel 5. The probe tip 17 and the rest of the data collection probe 7 are pulled through the lumen 11 such that the tip passes through the stented region spanning side branch SB. As shown in FIG. 1B, a probe 7 is shown prior to or after insertion in a blood vessel. The probe 7 is in optical communication with an OCT system 10. The OCT system or subsystem 10 that connects to probe 7 via an optical fiber 15 can include a light source such as a laser, an interferometer having a sample arm and a reference arm, various optical paths, a clock generator, photodiodes, and other OCT system components.

In one embodiment, an optical receiver 31 such as a balanced photodiode based system can receive light exiting the probe 7. A computing device 40 such as a computer, processor, ASIC or other device can be part of the OCT system 10 or can be included as a separate subsystem in electrical or optical communication with the OCT system 10. The computing device 40 can include memory, storage, buses and other components suitable for processing data and software 44 such as image data processing stages configured for side branch detection, stent strut candidate selection or identification, stent strut validation, correlations and comparisons of stent image data stent visualization, and pullback data collection as discussed below. In one embodiment, the software 44 can include a pipeline that includes various modules such as a jailed side branch/stent detection module. The module can include various other software modules such as a sparse peak detection module, model strut generation module, false positive testing module, and others as described herein.

In one embodiment, the computing device 40 includes or accesses software modules or programs 44, such as a side branch detection module, a lumen detection module, a stent detection module, a stent strut validation module, a candidate stent strut identification module and other software modules. The software modules or programs 44 can include an image data processing pipeline or component modules thereof and one or more graphical user interfaces (GUI). The modules can be subsets of each other and arranged and connected through various inputs, outputs, and data classes.

An exemplary image processing pipeline and components thereof can constitute one or more of the programs 44. The software modules or programs 44 receive image data and transform such image data into two dimensional and three dimensional views of blood vessels and stents can include lumen detection software module, peak detection, stent detection software module, side branch detection software module and a jailed or blocked side branch module. The image data processing pipeline, its components software modules and related methods and any of the methods described herein are stored in memory and executed using one or more computing devices such as a processor, device, or other integrated circuit.

Figure 1C:
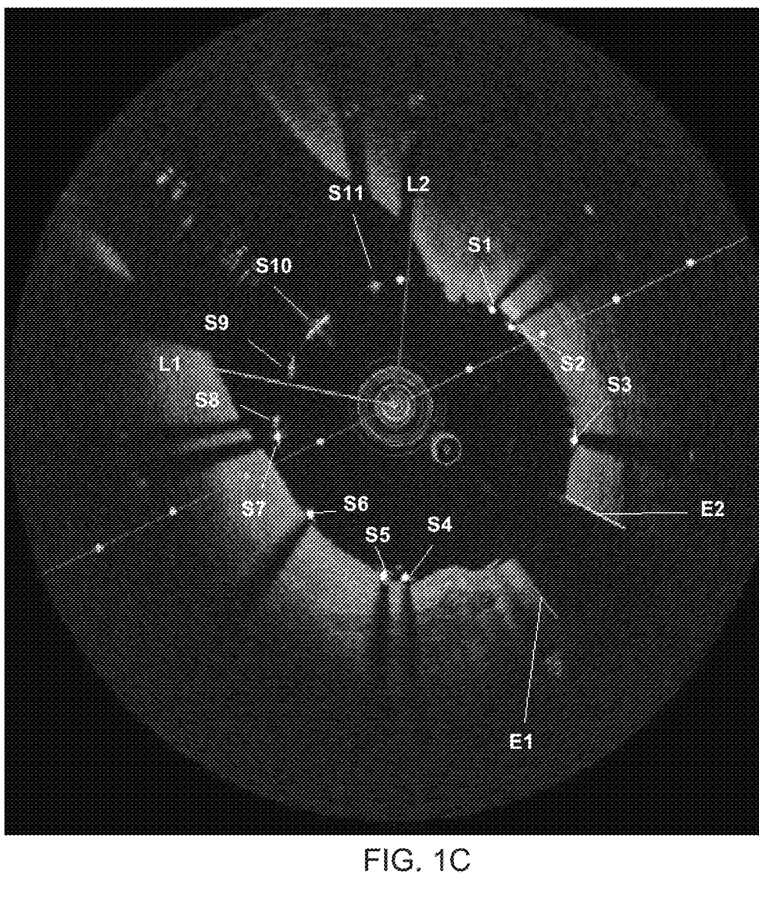
FIG. 1C is a cross-sectional OCT image of a stented blood vessel that includes a non-oblique jailed side branch according to an illustrative embodiment of the disclosure.

As shown, in FIG. 1A, a display 46 can also be part of the system 10 for showing information 47 such as cross-sectional and longitudinal views of a blood vessel generated using collected image data. Representations of a stent and a side branch such as OCT or IVUS images thereof can be shown to a user via display 46. Side branch detection and stent detection are performed prior to the display of these features and any coding or tagging with identifying indicia that may be included in the displayed image. This OCT-based information 47 can be displayed using one or more graphic user interface(s) (GUI). The images of FIGS. 1B and 1C are examples of information 47 that can be displayed and interacted with using a GUI and various input devices.

In addition, this information 47 can include, without limitation, cross-sectional scan data, longitudinal scans, diameter graphs, image masks, stents, areas of malapposition, lumen border, and other images or representations of a blood vessel or the underlying distance measurements obtained using an OCT system and data collection probe. The computing device 40 can also include software or programs 44, which can be stored in one or more memory devices 45, configured to identify stent struts and malapposition levels (such as based on a threshold and measured distance comparison) and other blood vessel features such as with text, arrows, color coding, highlighting, contour lines, or other suitable human or machine readable indicia.

Once the OCT data is obtained with a probe and stored in memory; it can be processed to generate information 47 such as a cross-sectional, a longitudinal, and/or a three-dimensional view of the blood vessel along the length of the pullback region or a subset thereof. These views can be depicted as part of a user interface as shown in FIGS. 1B and 1C and as otherwise described herein.

FIG. 1B is a cross-sectional image of a stented blood vessel obtained using an intravascular imaging probe, in this example, an OCT probe. The lumen of the main blood vessel 11 is demarcated by a dashed ellipse as shown. A large side branch SB joins the main vessel at an oblique angle. The side branch lumen appears as a dark void in the OCT image data. The side branch opening is demarcated by lines SBa and SBb. Line SBa has been annotated with X shaped indicia and line SBb has been annotated with O shaped indicia. The sidewall of the side branch 14 is detectable in the OCT image because the side branch joins the main vessel at an oblique angle. A large strut shadow 16 is also shown in the image of FIG. 1B. Side branch SB in the cross-sectional image of FIG. 1B can correspond to side branch SB in FIG. 1A in one embodiment.

Also visible in FIG. 1B are jailing stent struts 18 which were detected in accordance with the present invention. Side branch SB is occluded by multiple jailing struts 18. These jailing struts would be undetectable using shadow-based strut detection methods because the jailing struts overlie side branch voids.

In FIG. 1B the struts might indeed be detected via the shadow method, as the shadows are still visible against the back wall of the branch due to the oblique angle of departure for the side branch. In contrast, FIG. 1C contains struts which are likely not detectable using shadow detection based techniques. In FIG. 1C, struts S9 and S11 are possible to detect via shadow technique (although not guaranteed), but S10 is undetectable via shadow techniques as there is no shadow.

Thus, there are no shadows associated with these struts in OCT image data. However, using the detection methods described herein, these jailing struts are detectable. FIG. 1C is an intravascular image generated using an OCT probe and an intravascular data collection and analysis system.

The image of FIG. 1C shows an example of a non-oblique side branch, in which the side branch departs from the main branch at an angle close to 90 degrees, and in which struts are detected relative to a side branch and otherwise as shown. User interface lines L1 and L2 are shown radiating out from the intravascular probe and bound a side branch. Stent struts S1 to S11 are shown around the lumen border. Struts S8, S9, S10 and S11 are jailing a side branch as shown. The image processing and validation steps described herein increase the sensitivity and accuracy of the detection of these types of jailing struts in the side branch orientation shown and others. The edges of a shadow are shown by E1 and E2.

Once detected, the struts can be displayed on a user interface, which conveys vital information to the clinician about the precise location of stent struts and whether adjustments may be necessary to optimize stent placement and reduce the risk of side effects. The presence of jailing struts over a side branch is an important input for treatment, and in some cases additional interventions can be executed to mitigate the negative effects resulting from the jailed sidebranch. The user interface can include cross-sectional images, L-Mode images, A-Line images, three dimensional renderings, or any other suitable display format for visualizing detected struts.

At a high level, the methods disclosed herein detect jailing struts in OCT image data by detecting bright spots that are bordered by dark regions. Stent struts, and bare metal stent struts in particular, reflect the coherent light used in OCT imaging. The methods described herein can be used with stent struts that can be detected in an intravascular image. In one embodiment, the struts are metal struts such as bare metal struts "BMS" for example. However, blood vessel tissues, lipid plaques, and other intravascular features also reflect coherent light, making it difficult to distinguish struts in OCT images based on reflectivity alone. Further, as noted above, shadows cast by jailing struts are not detectable against the backdrop of a side branch lumen. To solve this problem, an algorithm called Naïve Peak at Line Measurement (NPLM) is provided for detecting jailing struts.

Figure 2A:
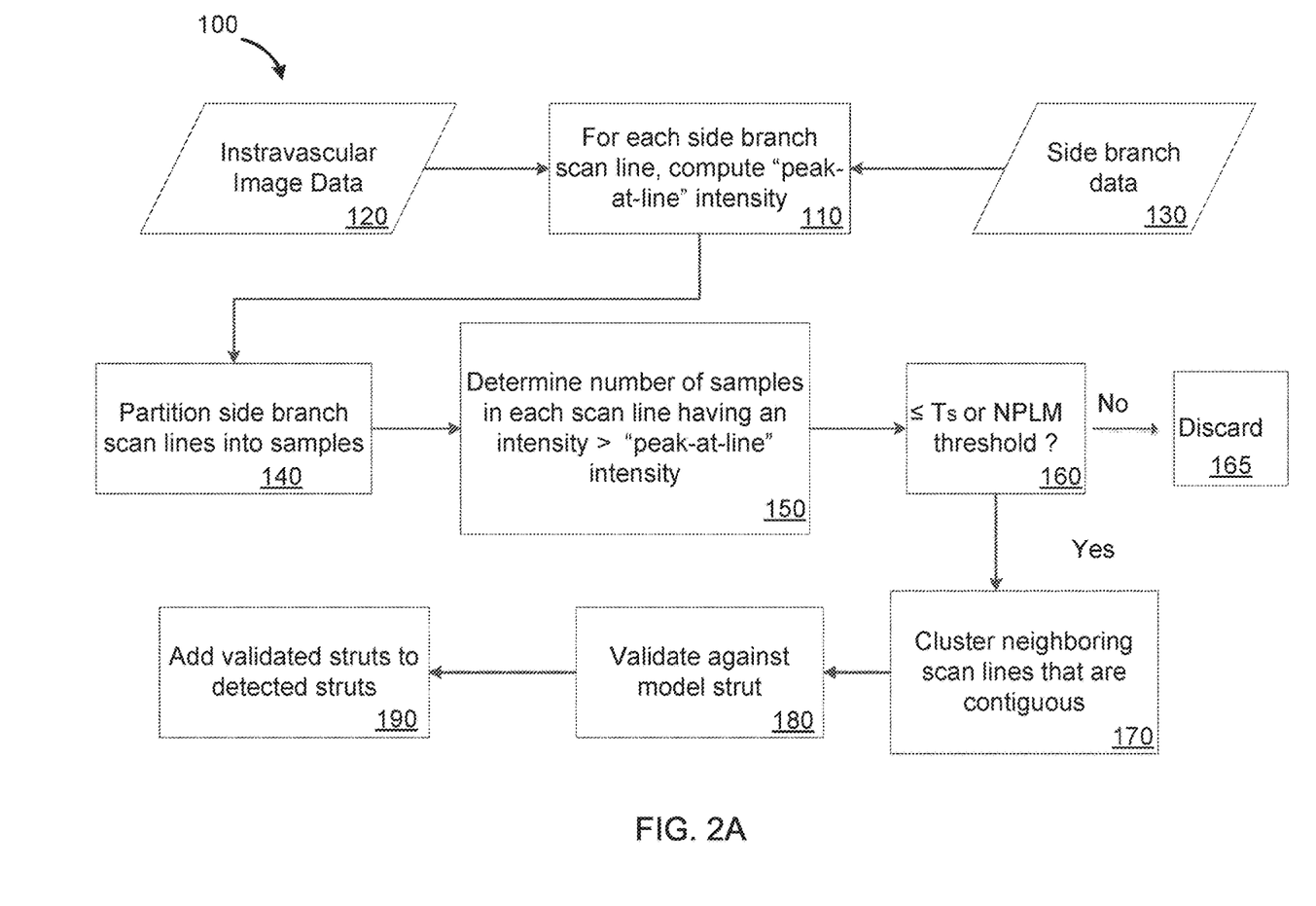
FIG. 2A is a process flow chart for detecting jailing struts in OCT image data and FIG. 2B is process flow chart of a method of detecting a stent strut in a representation of a blood vessel according to an illustrative embodiment of the disclosure.
Figure 2B:
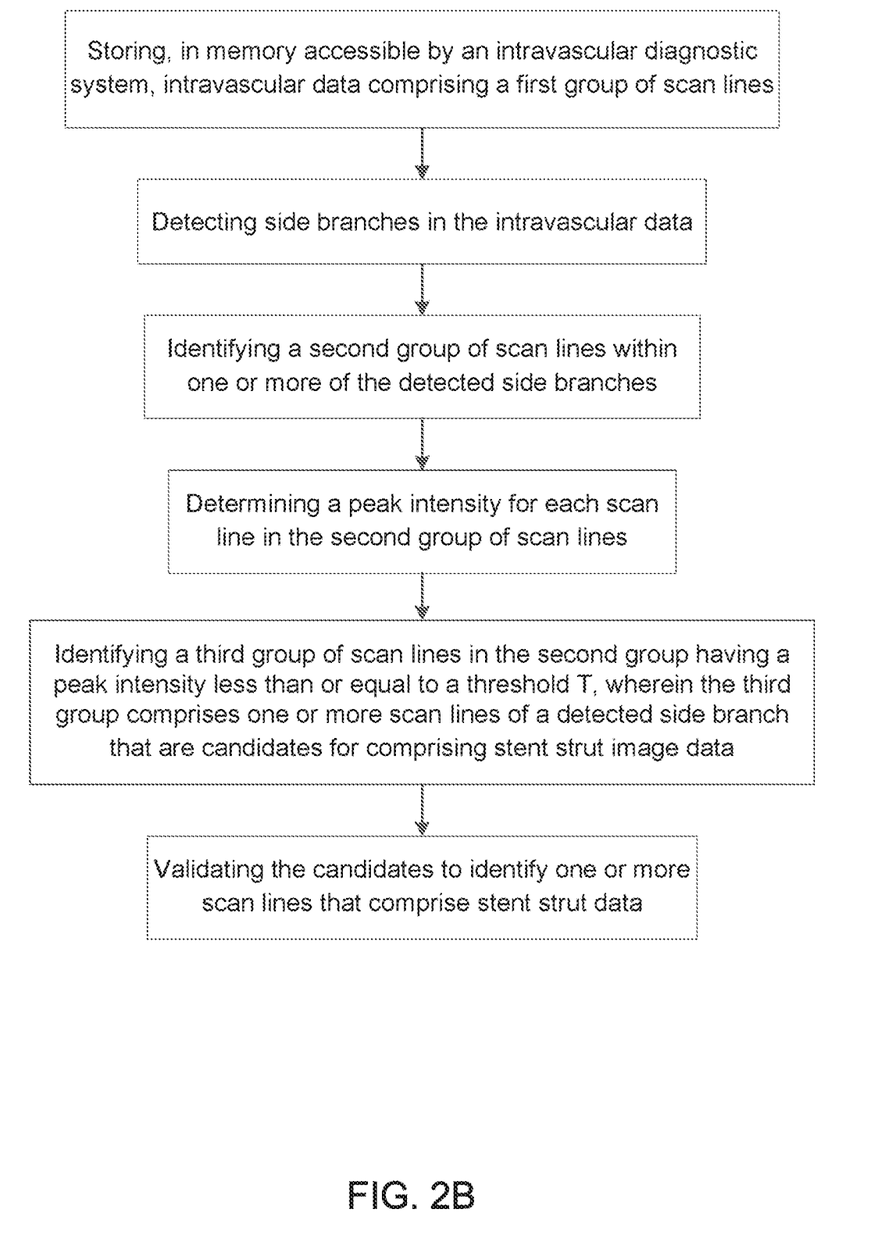

FIG. 2A is a process flow chart for detecting jailing struts in OCT image data. The stent strut threshold T or NPLM algorithm 100 is based on the observation that OCT scan lines, or A-Lines, of jailing struts are essentially sparse peaks at the strut locations. That is, the scan line reflects back at different intensities, with the strut appearing bright against the dark backdrop of the side branch. In preferred embodiments, only scan lines beyond the catheter are analyzed because the catheter can interfere with the detection process. The methods and systems of the invention can include one or more of the steps described herein. Unless otherwise required, the steps may be performed in any order. Other thresholds T can be used in lieu of or in addition to NPLM threshold.

The first step 110 of the method 100 is to compute the peak-at-line intensity (i.e., maximum intensity) for each scan line that corresponds to a side branch in the pullback data. Scan lines corresponding side branches are extracted from the original, raw image data 120 and side branch data 130 gathered during the imaging process. The raw image data can be of various types and formats. For example, the raw image data can be scan lines, 8 bit data, 16 bit data, 32 bit data, and other data formats. The original, raw image data 120 include the OCT scan lines. The side branch data 130 include the locations of side branches in the OCT pullback. Methods, systems, and devices for detecting side branches are known such as described in U.S. Pat. No. 8,831,321, the contents of which are incorporated by reference in its entirety.

At Step 140, each side branch scan line is partitioned into a plurality of "samples", and the samples are subsequently analyzed for brightness. In one embodiment, the analysis uses the portion of the scan-line beyond the imaging catheter and up to a certain depth beyond the sidebranch ostium (if known).

At Step 150, the samples are analyzed to count those samples with intensity above a pre-determined threshold on an image statistic along the scan-line. The threshold on the selected image statistic can vary for each scan line. For example, the threshold intensity can be a function of the maximum peak intensity for a given scan line, and samples from that scan line can be compared against the scan-line-specific peak intensity. Alternatively, the same threshold intensity can be used to analyze samples from different scan lines.

In one embodiment, the threshold intensity is scan-line-specific and corresponds to the peak intensity detected at the scan-line, and samples from a given scan line are screened to identify the number of samples having an intensity greater than about 10% of the peak-at-line intensity (i.e., 0.1×peak-at-line) for that particular scan line. In one embodiment, the screening of the samples to limit the result to a threshold proportional to the peak-at-line intensity generates a result that is equivalent to the maximum peak on that line. In one embodiment, the threshold varies for each scanline. In one embodiment, the measurement of peak intensity varies from scanline to scanline which yields a threshold value.

At Step 160, the number of samples calculated in Step 150 is compared against an empirically determined threshold, or NPLM threshold. The NPLM threshold is based on an upper bound on the strut blooming manifested on the OCT image. In one embodiment, the NPLM threshold is set on a per imaging system basis. The threshold can be set empirically by establishing a sensitivity level and adjusting the parameters of the strut detection method accordingly. If the number of samples calculated in Step 150 is less than or equal to the NPLM threshold, then the scan line is flagged as containing a potential strut and the process continues to Step 170.

As noted above, jailing struts appear as sparse peaks in the scan lines against the dark backdrop of side branches. The NPLM threshold tests the scan line profile to confirm the sharpness and overall width of an intensity peak(s). If too many samples exceed the threshold, then the "no" path is followed to Step 165 in which the scan line is then discarded as likely not containing a jailing strut or it is penalized (i.e., set aside) until/unless it is apparent that the penalized scan line is part of a continuous block of flagged scan lines.

At Step 170, neighboring flagged scan lines are clustered into contiguous blocks. The strut region is defined as a number of consecutive scan lines that qualified under the NPLM threshold. A tentative final location (in terms of A-Line and offset) is also determined for each strut.

At Step 180, after identifying potential struts and their locations, struts optionally can be vetted to determine whether they are true positives or false positives. In various embodiments, the line profile of a detected strut is compared to the profile of a "model" strut at the detected location using a linear correlation coefficient as the comparison metric. A model strut profile is created as a sharp peak with the same peak intensity as the detected strut and at the same location on the scan line as the detected strut. Correlation coefficients measure the association or similarity between two vectors or variables. Here, the correlation coefficient is defined as:

$$r_{xy} = \frac{\sum_{i=1}^{N}(x_i - \mu_x)(y_i - \mu_y)}{\sigma_x \sigma_y}$$

where, $\gamma_{xy}$ is the correlation coefficient between measurements x and y are the measurements, x corresponds to the detected potential strut and y corresponds to the model strut.

$\mu_x$ and $\mu_y$ are the respective means of those measurements, and $\sigma_x$ and $\sigma_y$ are the respective standard deviations of those measurements.

If the correlation coefficient is greater than an empirically determined threshold, which is determined based on multiple datasets and experimental analysis, then the detected strut is deemed a true positive and are added to a list of detected struts (Step 190). If the correlation coefficient is less than an empirically determined threshold, then the detected strut is penalized or discarded.

Figure 3A:
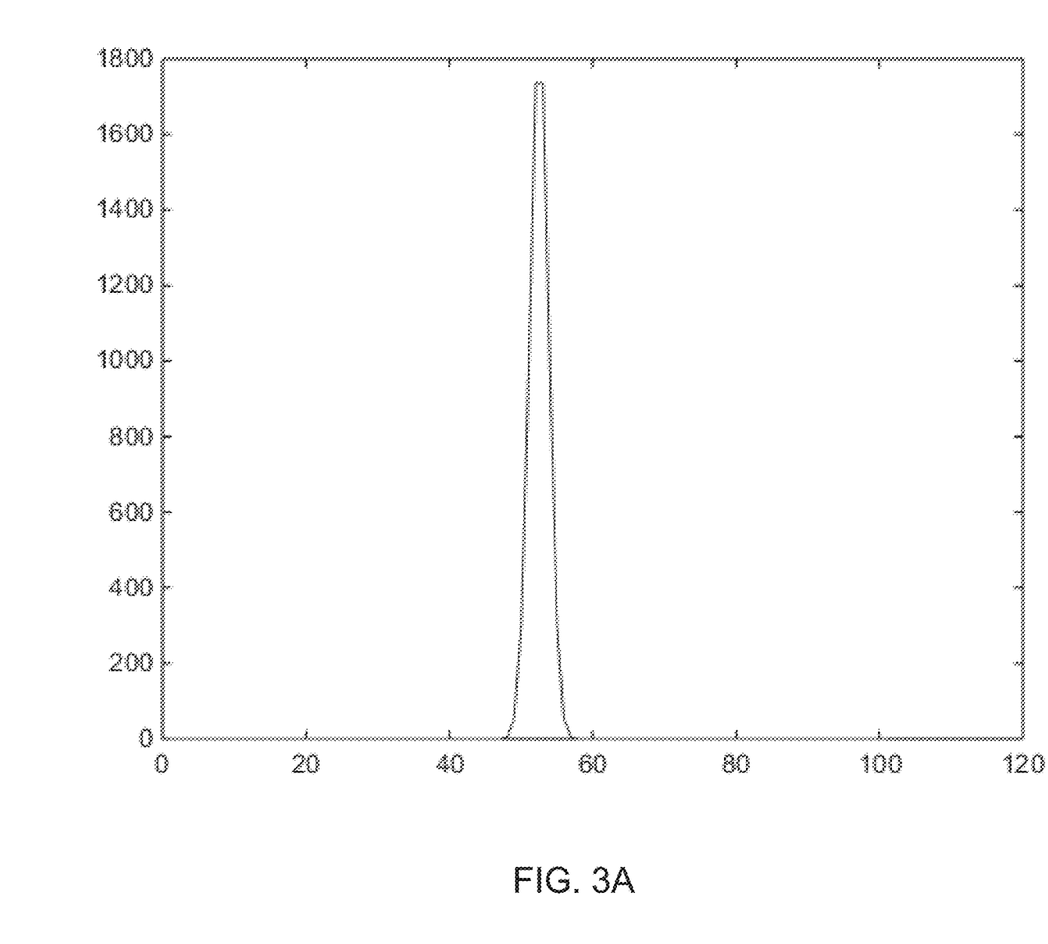
FIG. 3A is a graph illustrating a model strut according to an illustrative embodiment of the disclosure.
Figure 3B:
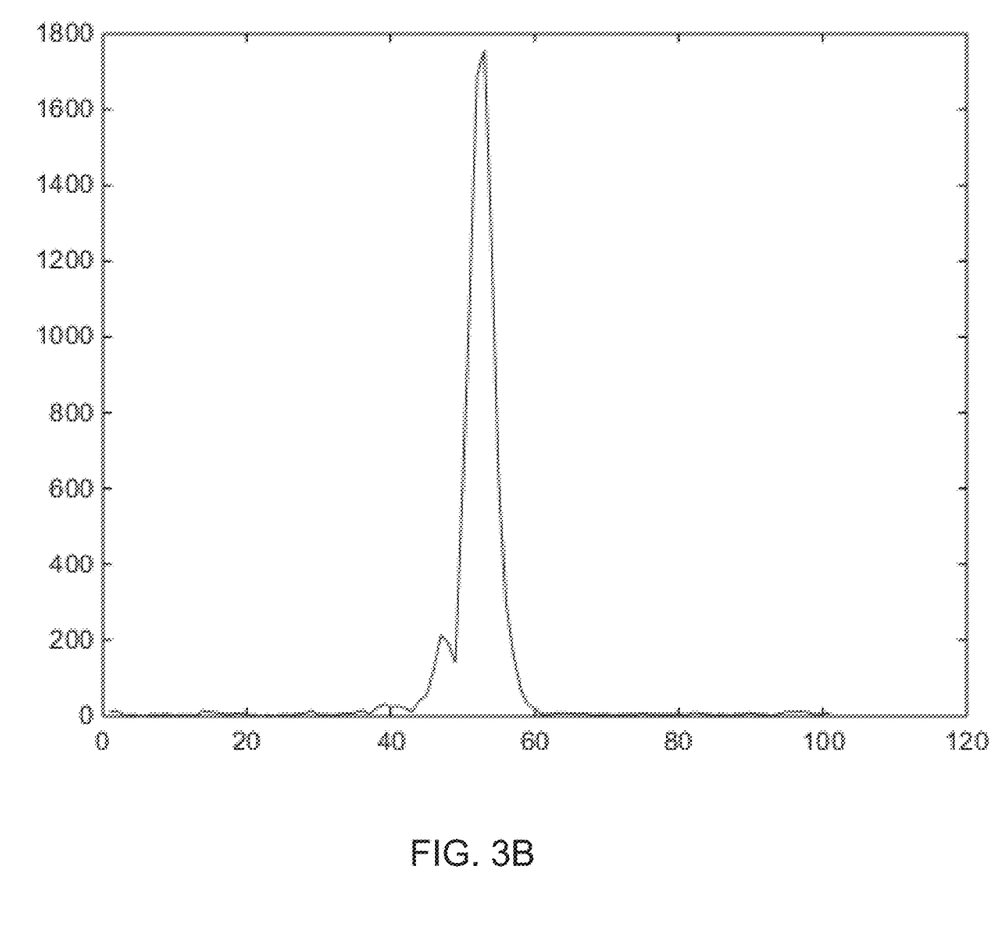
FIG. 3B is a graph illustrating detection of a true strut according to an illustrative embodiment of the disclosure.
Figure 3C:
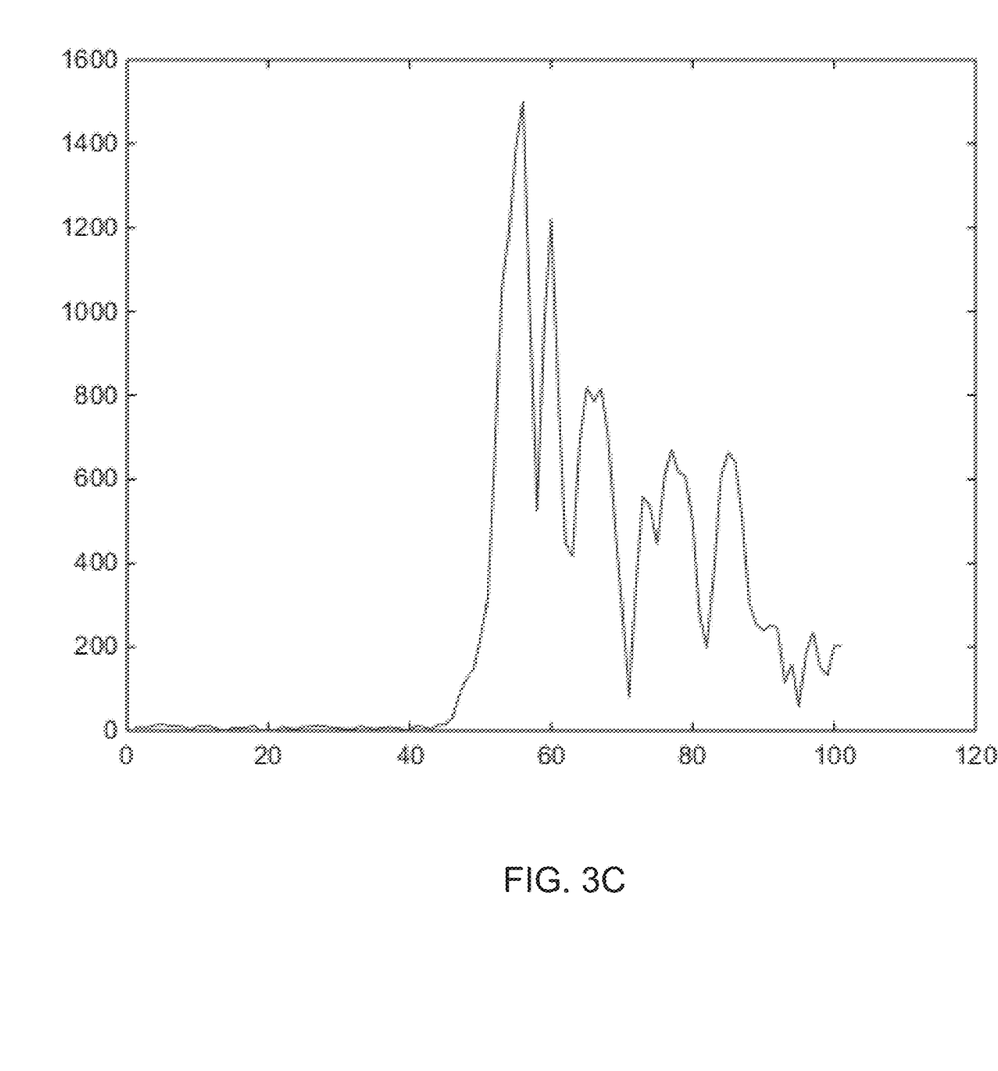
FIG. 3C is a graph illustrating detection of a false positive strut in a blood vessel lumen according to an illustrative embodiment of the disclosure.
Figure 3D:
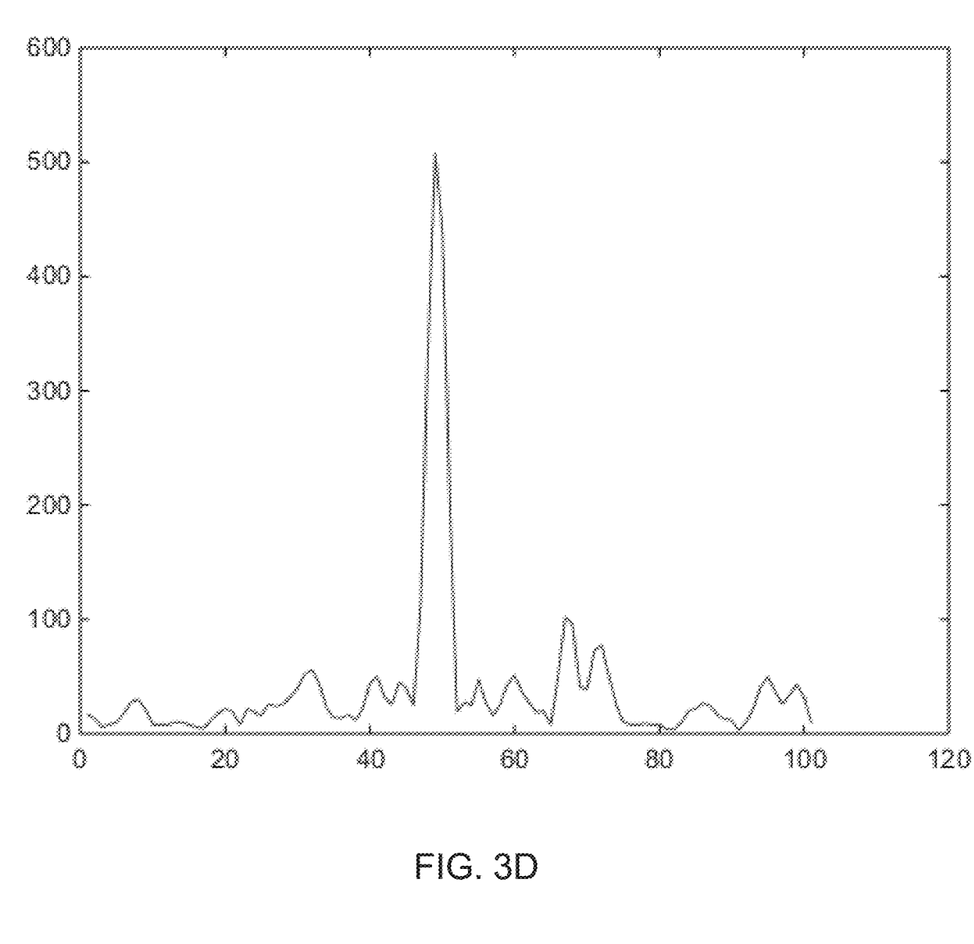
FIG. 3D is a graph illustrating detection of a false positive strut in blood according to an illustrative embodiment of the disclosure.

FIGS. 3A-D are validation graphs plotting signal intensity versus strut location. FIG. 3A is a graph illustrating a model strut profile. X axis corresponds to the samples along the scan-line. Y axis corresponds to the strut intensity. The shape of a true strut profile typically is the same as the model strut profile and therefore, bears a high correlation with the model strut., FIG. 3B is a graph illustrating detection of a true strut. The peak shape of the true positive strut is similar to the model peak. FIG. 3C is a graph illustrating detection of a false positive strut detected in the blood vessel lumen. In contrast to FIGS. 3A and 3B, FIG. 3C shows a significant amount of signal to the right of the main peak. Consequently, a potential strut detected in the blood vessel lumen with a profile shown in FIG. 3C would have a low correlation to the model strut and would be discarded as a false positive. FIG. 3D is a graph illustrating another false positive strut caused by blood cells within the lumen. Here too, the correlation of the potential strut profile with respect to the model strut falls below the allowed threshold, and hence this too gets discarded as a false positive.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below.

Embodiments of the invention may be implemented in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present invention, some or all of the processing of the data collected using an OCT probe, an FFR probe, an angiography system, and other imaging and subject monitoring devices and the processor-based system is implemented as a set of computer program instructions that is converted into a computer executable form, stored as such in a computer readable medium, and executed by a microprocessor under the control of an operating system. Thus, user interface instructions, detection steps and triggers based upon the completion of a pullback or a co-registration request, for example, are transformed into processor understandable instructions suitable for generating OCT data, detecting struts, validating struts, display detected and validated struts and performing image procession using various and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Various examples of suitable processing modules are discussed below in more detail. As used herein a module refers to software, hardware, or firmware suitable for performing a specific data processing or data transmission task. In one embodiment, a module refers to a software routine, program, or other memory resident application suitable for receiving, transforming, routing and processing instructions, or various types of data such as angiography data, OCT data, IVUS data, peak intensity, adaptive thresholds, and other information of interest as described herein.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the invention.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

The invention claimed is:

1. A method of detecting one or more stent struts disposed in a side branch, the method comprising:
   storing, in memory accessible by a diagnostic system, one or more image datasets obtained with respect to a blood vessel;

detecting, using a side branch detection module of the diagnostic system, one or more side branches of the blood vessel using the one or more image datasets;

identifying side branch image data corresponding to each detected side branch, wherein each side branch has a shadow region;

determining one or more candidate intensity peaks relative to one or more shadow regions; and validating the one or more candidate intensity peaks, wherein each valid intensity peak corresponds to a portion of a stent strut jailing one or more side branches.

2. The method of claim 1, further comprising generating a representation of the blood vessel and displaying regions of the blood vessel identified as corresponding to a jailed side branch using one or more indicia.

3. The method of claim 1, wherein the validating step comprises determining if each candidate is a false positive.

4. The method of claim 3, wherein determining if each candidate is a false positive comprises comparing candidate stent strut image data to model stent strut image data.

5. The method of claim 1, wherein the validating step comprises comparing candidate stent strut image data to model stent strut image data using a correlation factor.

6. The method of claim 1 wherein the one or more image datasets comprises scanlines, wherein the scan lines are obtained using intravascular imaging.

7. The method of claim 6 further comprising clustering neighboring scan lines that are contiguous, before validating against the model strut.

8. The method of claim 6 further comprising identifying number of samples for each scan line having a peak intensity less than or equal to a threshold T as a candidate scan line for containing a metal strut in a side branch.

9. The method of claim 1 further comprising determining a start frame and an end frame for each side branch.

10. An automatic processor-based diagnostic system for detecting one or more stent struts disposed in a side branch, the system comprising:

one or more memory devices; and a computing device in communication with the memory device, wherein the memory device comprises instructions executable by the computing device to cause the computing device to:

store, in the one or more memory devices, one or more image datasets obtained with respect to a blood vessel;

detect, using a side branch detection module of the diagnostic system, one or more side branches of the blood vessel using the one or more image datasets;

identify side branch image data corresponding to each detected side branch, wherein each side branch has a shadow region;

determine one or more candidate intensity peaks relative to one or more shadow regions; and validate the one or more candidate intensity peaks, wherein each valid intensity peak corresponds to a portion of a stent strut jailing one or more side branches.

11. The system of claim 10 wherein the computing device comprises further instructions to cause the computing device to generate a representation of the blood vessel and displaying regions of the blood vessel identified as corresponding to a jailed side branch using one or more indicia.

12. The system of claim 10 wherein instructions to validate comprise determining if each candidate is a false positive.

13. The system of claim 12, wherein determining if each candidate is a false positive comprises comparing candidate stent strut image data to model stent strut image data.

14. The system of claim 10 wherein instructions to validate comprise comparing the candidate stent strut image data to model stent strut image data using a correlation factor.

15. The system of claim 10 wherein the one or more image datasets comprises scanlines, wherein the scan lines are obtained using intravascular imaging.

16. The system of claim 15 wherein the computing device comprises further instructions to cause the computing device to cluster neighboring scan lines that are contiguous, before validating against the model strut.

17. The system of claim 10 wherein the computing device comprises further instructions to cause the computing device to identify number of samples for each scan line having a peak intensity less than or equal to a threshold T as a candidate scan line for containing a metal strut in a side branch.

18. The system of claim 17 wherein if the number of samples having an intensity >peak-at-line intensity is greater than threshold T for a candidate strut, discarding the candidate strut or the scan line comprising the candidate strut.

19. The system of claim 10 wherein the computing device comprises further instructions to cause the computing device to determine a start frame and an end frame for each side branch.

* * * * *